(12) United States Patent
Molloy et al.

(10) Patent No.: US 12,708,798 B2
(45) Date of Patent: Aug. 18, 2026

(54) QUALITY ASSURANCE SYSTEM AND METHOD

(71) Applicant: UNIVERSITY OF KENTUCKY RESEARCH FOUNDATION, Lexington, KY (US)

(72) Inventors: Janelle A. Molloy, Nicholasville, KY (US); Allison Palmiero, Nicholasville, KY (US); Justin Visak, Nicholasville, KY (US)

(73) Assignee: University of Kentucky Research Foundation, Lexington, KY (US)

( * ) Notice: Subject to any disclaimer, the term of this patent is extended or adjusted under 35 U.S.C. 154(b) by 248 days.

(21) Appl. No.: 18/688,945

(22) PCT Filed: Sep. 29, 2022

(86) PCT No.: PCT/US2022/045136
§ 371 (c)(1),
(2) Date: Mar. 4, 2024

(87) PCT Pub. No.: WO2023/055870
PCT Pub. Date: Apr. 6, 2023

(65) Prior Publication Data

US 2024/0382781 A1 Nov. 21, 2024

Related U.S. Application Data

(60) Provisional application No. 63/251,278, filed on Oct. 1, 2021, provisional application No. 63/249,657, filed on Sep. 29, 2021.

(51) Int. Cl.
*A61N 5/10* (2006.01)

(52) U.S. Cl.
CPC .................................. *A61N 5/1075* (2013.01)

(58) Field of Classification Search
None
See application file for complete search history.

(56) References Cited

U.S. PATENT DOCUMENTS 5,077,768 A * 12/1991 Shigyo .................. G01T 1/2012 378/62
5,142,559 A * 8/1992 Wielopolski ......... A61N 5/1075 378/65
6,267,502 B1 7/2001 McNeirney et al.
7,339,159 B2 3/2008 Juh et al.
2007/0223651 A1 9/2007 Wagenaar et al.
2019/0239753 A1* 8/2019 Wentz .................. G01J 3/2803

FOREIGN PATENT DOCUMENTS

WO WO2020146086 A1 7/2020

* cited by examiner

*Primary Examiner* — Hoon K Song
(74) *Attorney, Agent, or Firm* — Stites & Harbison PLLC; Warren D. Schickli

(57) ABSTRACT

A quality assurance system for a medical accelerator includes a housing, an image plate supported by the housing and an image capture assembly. The image plate is adapted to display a visible light field image and a radiation field generated by the medical accelerator. The image capture assembly is adapted to capture the visible light field image and the radiation field displayed by the image plate.

18 Claims, 11 Drawing Sheets

QUALITY ASSURANCE SYSTEM AND METHOD

RELATED APPLICATION

This application is a § 371 National State Application of PCT/US2022/045136 filed Sep. 29, 2022 which claims priority to U.S. Provisional Patent Application Ser. No. 63/249,657 filed on Sep. 29, 2021 and U.S. Provisional Patent Application Ser. No. 63/251,278 filed on Oct. 1, 2021, the full disclosure of which is hereby incorporated by reference.

GOVERNMENT SUPPORT

This invention was made with government support under Grant No. 1R43CA26141-01 awarded by the National Cancer Institute. The government has certain rights in the invention.

TECHNICAL FIELD

This document relates to a new quality assurance system and method designed for the measurement of a two-dimensional radiation fluence image in relation to visible and mechanical indicators. It is particularly suited for quality assurance of medical linear accelerators operating in the 6-18 MV energy range.

BACKGROUND

The new quality assurance system and method can be used to measure common medical accelerator QA metrics. The quality assurance system converts a radiation spatial pattern into visible light. In addition, the quality assurance system includes a calibration template that provides landmarks so that image distortion can be corrected, and the spatial calibration of the camera pixels can be determined.

The quality assurance system and related method are designed for the measurement of absorbed doses of ionizing radiation. The system and method are particularly suited for high-energy photons. More specifically, the quality assurance system and related method are designed for the measurement of a two-dimensional radiation fluence image in relation to visible and mechanical indicators. They are particularly suited for quality assurance of medical linear accelerators operating in the 6-18 MV energy range. They can be used to measure the coincidence of light and radiation fields, star shot patterns, and the position of the edges of radiation and light fields. The system and method may be capable of measuring radiation doses as small as 0.01 Gy, with effectively no upper limit. The quality assurance system is designed to remain stationary during data acquisition and does not connect with or alter the medical accelerator in any way. The system and method should be used by, or under the supervision, of a qualified medical physicist.

SUMMARY

In accordance with the purposes and benefits set forth herein, a new and improved quality assurance system is provided. That quality assurance system comprises, consists of or consists essentially of: (a) a housing, (b) an image plate supported by the housing wherein the image plate is adapted to display a visible light field image and a radiation field image generated by the medical accelerator and (c) an image capture assembly adapted to capture the visible light field image and the radiation field image displayed by the image plate. The system is a stand-alone, independent measurement tool that can be used to assess the radiation and mechanical stability of certain characteristics of a medical accelerator.

In one or more embodiments of the quality assurance system, the imaging plate includes a semi-transparent phosphor screen adapted to transmit the visible light field image generated by the medical accelerator through the semi-transparent phosphor screen as well as to convert the radiation field generated by the medical accelerator into a corresponding visible light image reproduction of the radiation field generated by the medical accelerator.

In one or more of the many possible embodiments of the quality assurance system, the image capture assembly is a small form factor optical tunnel (SFFOT). That SFFOT includes a lens, a mirror, an optical tunnel and a camera wherein (a) the lens focuses the visible light field image and the visible light image reproduction of the radiation field, (b) the mirror redirects the visible light field image and the visible light image reproduction of the radiation field from the lens through the optical tunnel, (c) the optical tunnel propagates the visible light field image and the visible light image reproduction of the radiation field from the mirror to the camera and (d) the camera captures the visible light field image and visible light image reproduction of the radiation field.

In one or more of the many possible embodiments of the quality assurance system, the housing further includes a removable lid that is displaceable between a radiation field image gathering position covering the image plate and a visible light field image gathering position exposing the image plate. The removable lid may be made from a radiation build up material. The housing, including the lid, and the optical tunnel may be opaque so as to prevent external, ambient visible light from entering the housing and the optical tunnel and thereby interfering with the display and image capturing of the visible light image reproduction of the radiation field generated by the medical accelerator.

In one or more of the many possible embodiments of the quality assurance system, the quality assurance system further includes a computing device adapted to do one or more of the following: (a) control the camera, (b) compare the visible light field image and the visible light image reproduction of the radiation field to determine proper coincidence, (c) display the visible light field image and the visible light image reproduction of the radiation field in real time and (d) collect and analyze data respecting the radiation field generated by the medical accelerator.

The quality assurance system may also include a calibration template that may be projected upon or physically placed upon the imaging plate.

The quality assurance system may also include a locator feature. That locator feature may comprise at least one locator window in a sidewall of the image plate wherein the at least one locator window is adapted to transmit laser light from an alignment laser of the medical accelerator onto the image plate. The at least one locator window may be exposed when the removable lid is in the visible light field gathering position and the at least one locator window is covered by the removable lid when the removable lid is in the radiation field image gathering position. In at least some embodiments of the quality assurance system, the locator feature further includes a prism associated with the at least one locator window and adapted to enhance the visibility of the laser light on the phosphor screen of the imaging plate.

In at least one of the many possible embodiments of the quality assurance system, the quality assurance system further includes alignment markings on the image plate, the housing or the image plate and the housing. Those alignment markings are adapted to allow for alignment of the image plate with the alignment laser or lasers of the medical accelerator.

In accordance with an additional aspect, a new and improved quality assurance system for a medical accelerator adapted to generate a visible light field and a radiation field comprises, consists of or consists essentially of: (a) a housing, (b) an image plate supported by the housing and (c) an image capture assembly. The housing further includes a removable lid that is displaceable between a radiation field image gathering position covering the image plate and a visible light field image gathering position exposing the image plate.

In at least one possible embodiment, the quality assurance system further includes a locator feature. That locator feature may comprise at least one locator window in a sidewall of the image plate, the housing or the image plate and the housing wherein the at least one locator window is adapted to transmit laser light from an alignment laser of the medical accelerator onto the image plate. The at least one locator window may be exposed when the removable lid is in the visible light field gathering position and the at least one locator window is covered by the removable lid when the removable lid is in the radiation field image gathering position. In at least some embodiments of the quality assurance system, the locator feature further includes a prism associated with the at least one locator window and adapted to enhance the visibility of the laser light on the phosphor screen of the imaging plate.

In accordance with still another aspect, a new and improved method is provided for assuring proper performance of a medical accelerator adapted to generate a visible light field and a radiation field. That method may be described as comprising, consisting of or consisting essentially of the steps of: (a) positioning a housing and an image plate of a quality assurance system in proper position on a couch of a medical accelerator by aligning alignment markings of the quality assurance system with alignment lasers of the medical accelerator, (b) displaying on the image plate a visible light field image and a radiation field image generated by the medical accelerator and (c) capturing the visible light field image and the radiation field image displayed by the image plate.

In one or more embodiments, the method may also include the step of transmitting the visible light field image generated by the medical accelerator through the image plate. In one or more embodiments, the method may also include the step of converting the radiation field image generated by the medical accelerator into a corresponding visible light image reproduction of the radiation field generated by the medical accelerator. Still further, the method may include the step of displacing a lid of the quality assurance system between a radiation field image gathering position covering the image plate and a visible light field image gathering position exposing the image plate.

In the following description, there are shown and described several preferred embodiments of the quality assurance system and the related method. As it should be realized, the system and method are capable of other, different embodiments and their several details are capable of modification in various, obvious aspects all without departing from the system and method as set forth and described in the following claims. Accordingly, the drawings and descriptions should be regarded as illustrative in nature and not as restrictive.

BRIEF DESCRIPTION OF THE DRAWING FIGURES

The accompanying drawing figures incorporated herein and forming a part of the specification, illustrate several aspects of the quality assurance system and the method and together with the description serve to explain certain principles thereof.

Figure 3A:
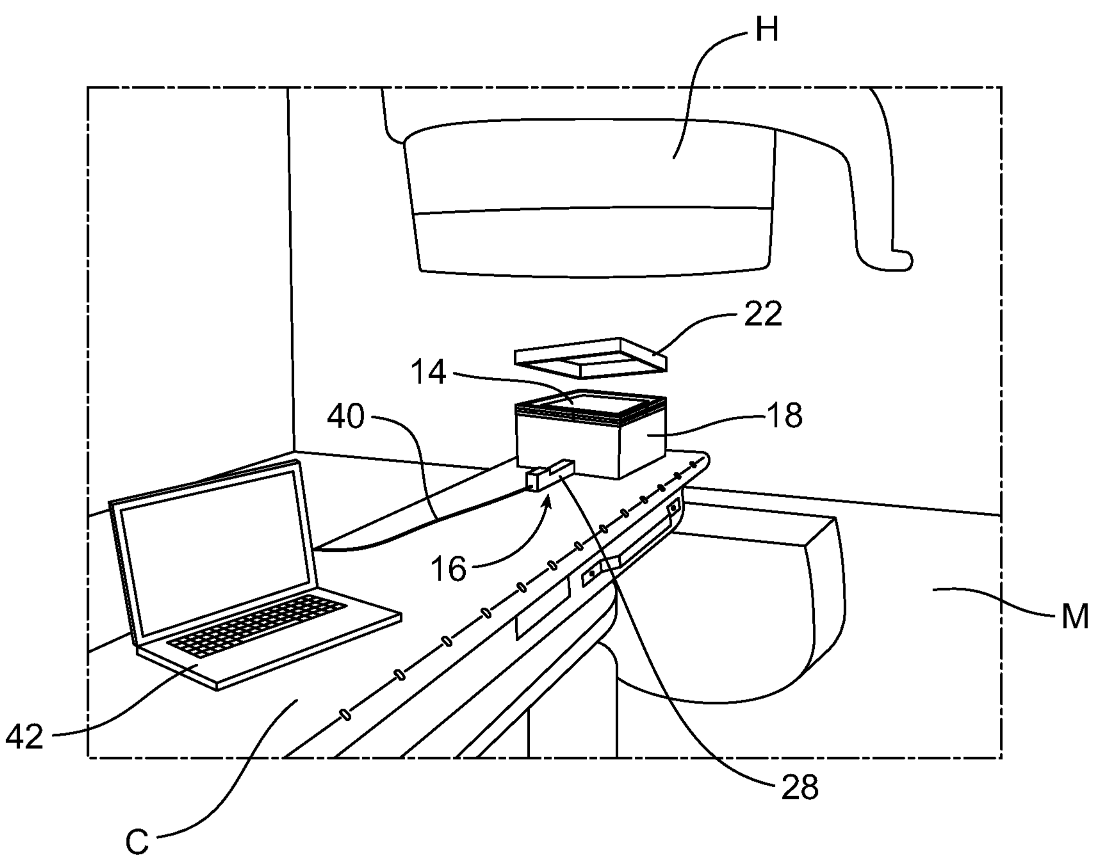
Figure 3B:
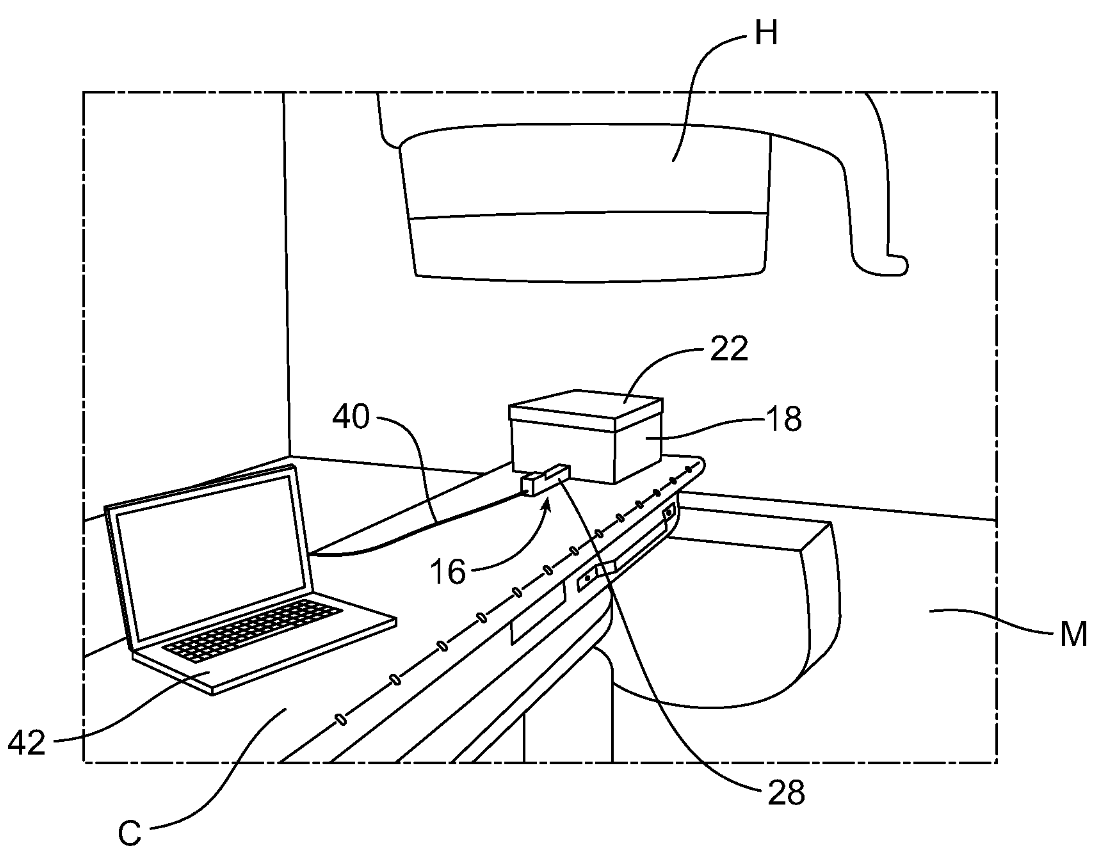

FIGS. 3A and 3B are perspective views of the new quality assurance system illustrating (a) the housing positioned on the couch under the gantry with the image plate at the radiation isocenter plane and (b) the image capture assembly connected to the computing device of the system via a signal cable. In FIG. 3A, the lid is removed so that the visible light field generated by the medical accelerator may be displayed on the image plate and captured by the camera of the image capture assembly. In FIG. 3B, the lid has been positioned on the housing over the image plate so that the radiation field generated by the medical accelerator may be converted by the image plate into a corresponding visible light image reproduction of the radiation field that is displayed on the image plate and captured by the camera.

Figure 4:
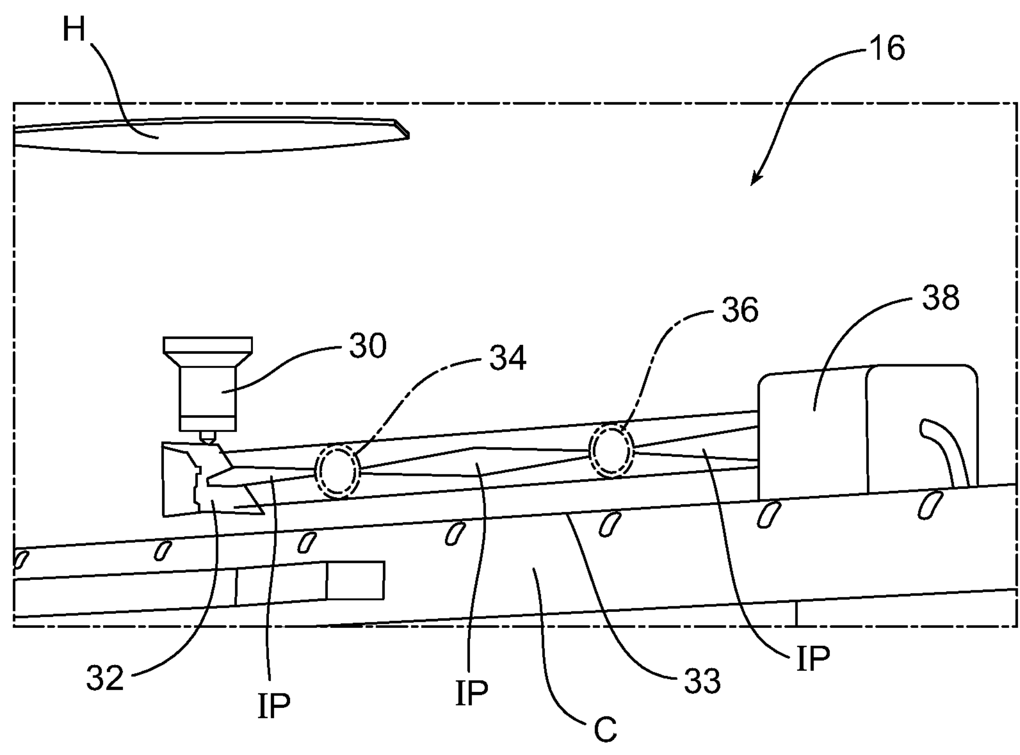

FIG. 4 is a schematic illustration of the optical components of the image capture assembly that are held inside the shroud or housing extension (shroud removed).

Figure 5:
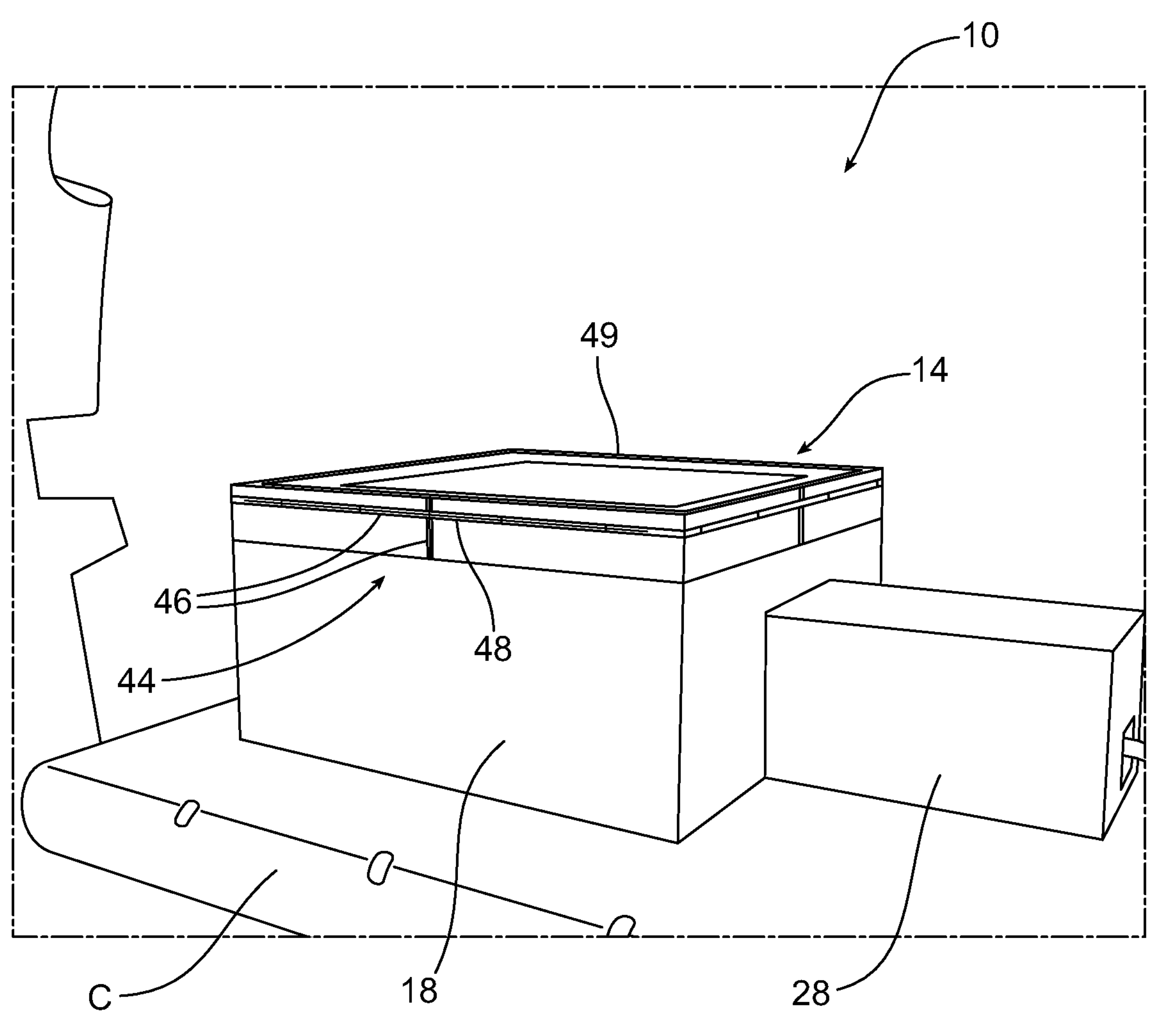

FIG. 5 is a detailed perspective view illustrating how the locator feature on the sides of the housing may be used to properly align the housing of the quality assurance system on the couch at the radiation isocenter plane.

Figure 6:
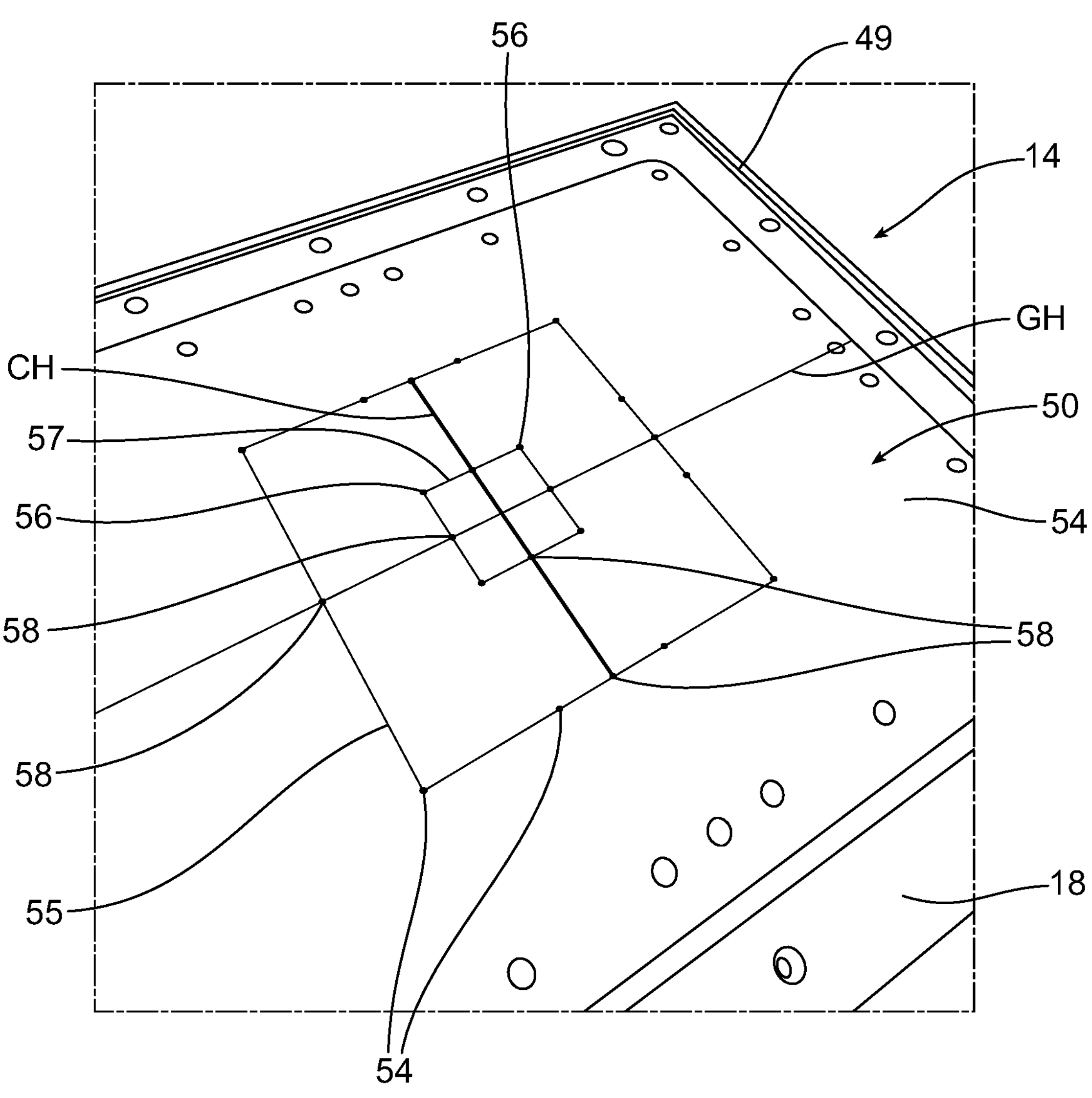

FIG. 6 is a perspective view illustrating the calibration template of the quality assurance system positioned on the image plate while a visible image of cross hairs is being projected downward from the gantry by the medical accelerator.

Figure 7:
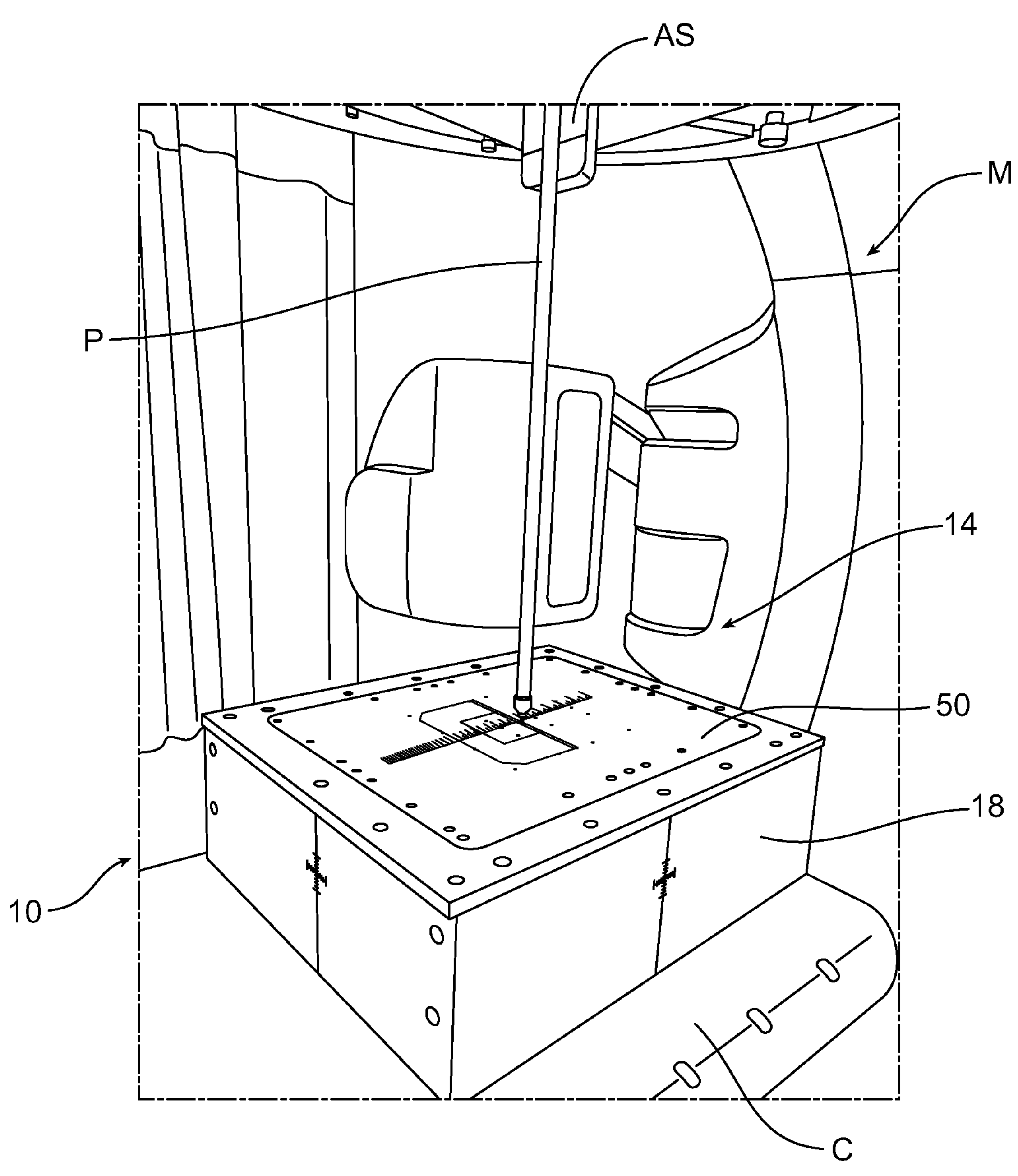

FIG. 7 is a perspective view illustrating how the front pointer is used to position the image plate at the SAD of the linac.

Figure 8A:
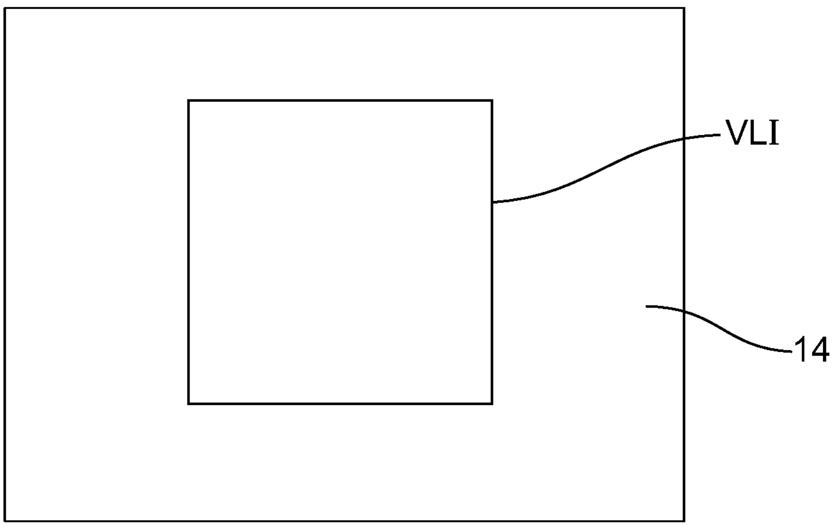

FIG. 8A is an illustration of a square visible light image of the radiation field as displayed toward the lens of the image capture assembly by the image plate.

Figure 8B:
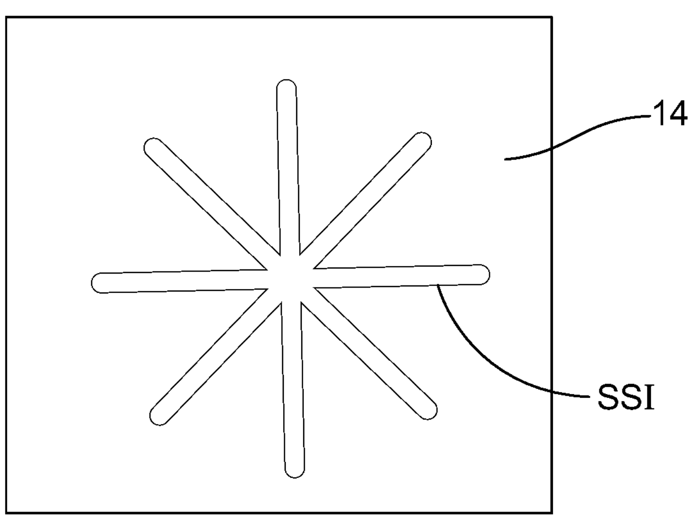

FIG. 8B is an illustration of a radiation star as displayed toward the lens of the image capture assembly by the image plate.

Figure 9:
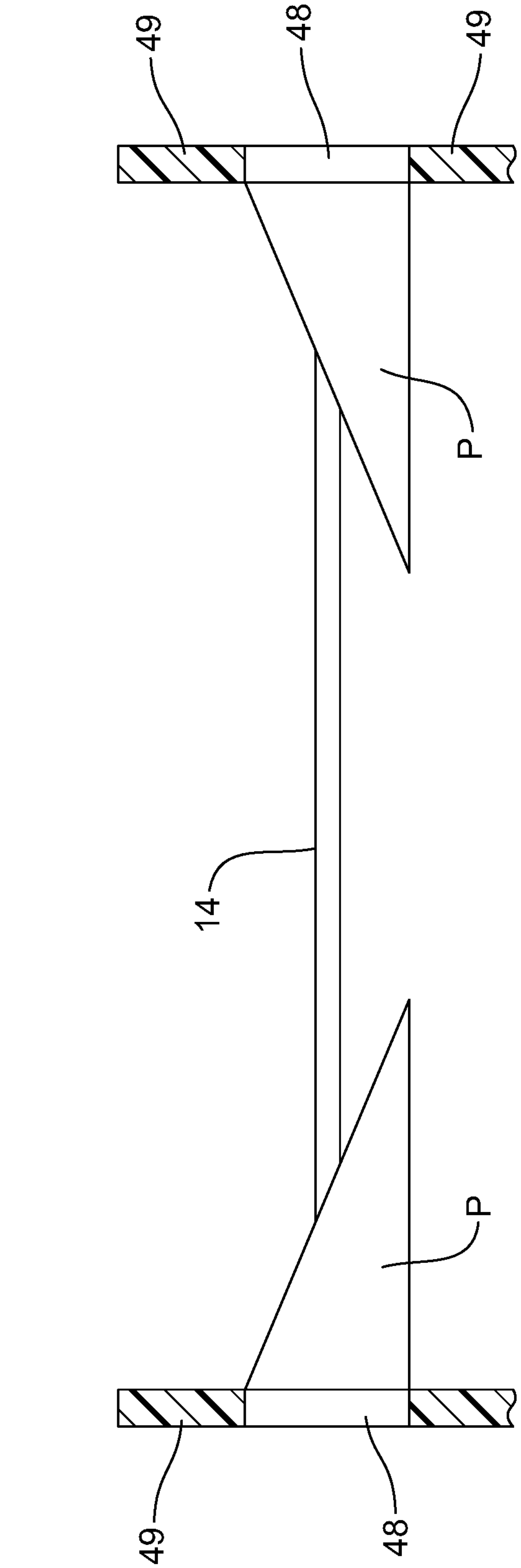

FIG. 9 is a schematic illustration of an alternative embodiment of the quality assurance system incorporating a prism between each locator window in the housing and the phosphor screen of the image plate.

DETAILED DESCRIPTION

Figure 1:
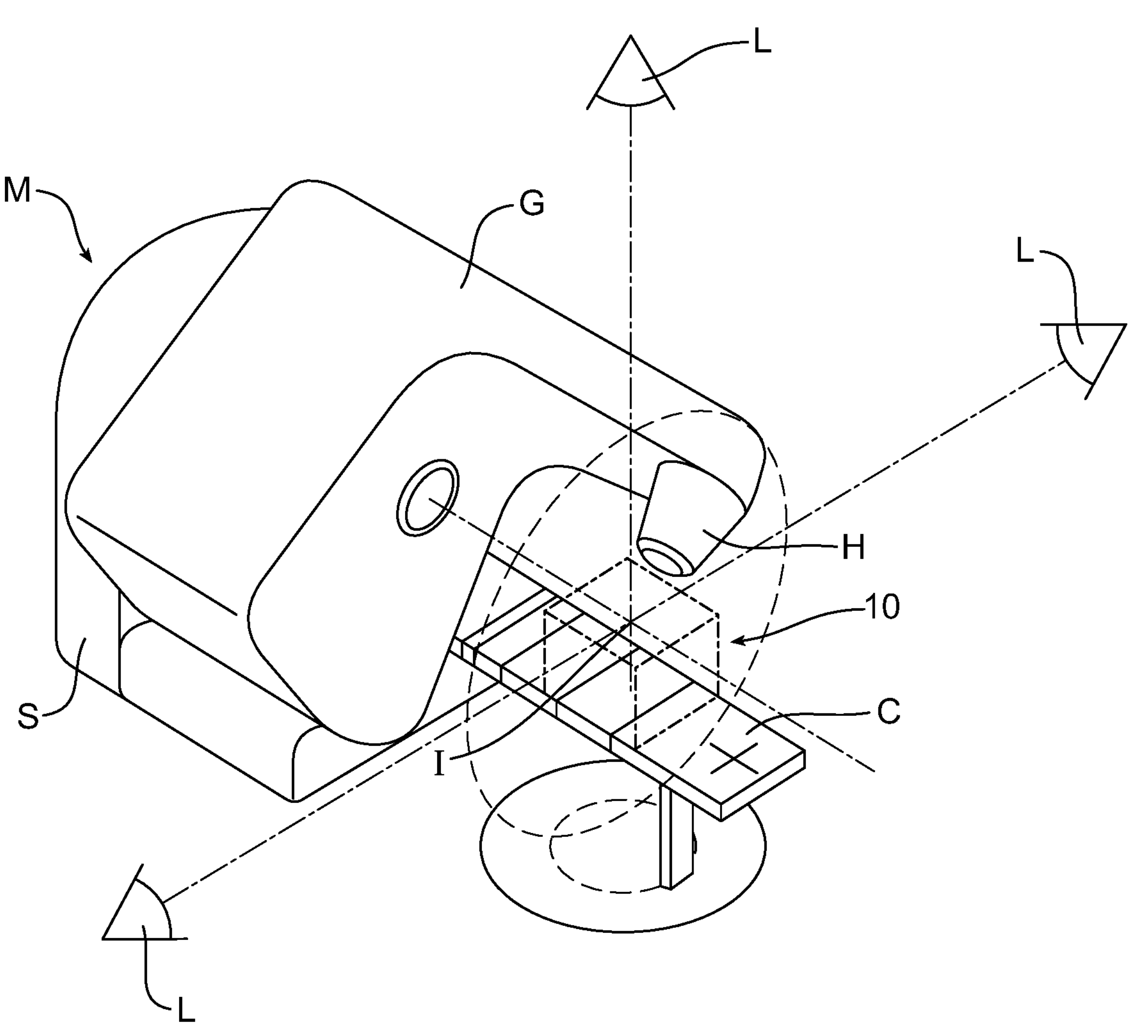
FIG. 1 is a perspective view of a medical accelerator that illustrates the quality assurance device housing positioned on the treatment couch, at the intersection of the room lasers, adjacent the gantry of the medical accelerator.
Figure 2:
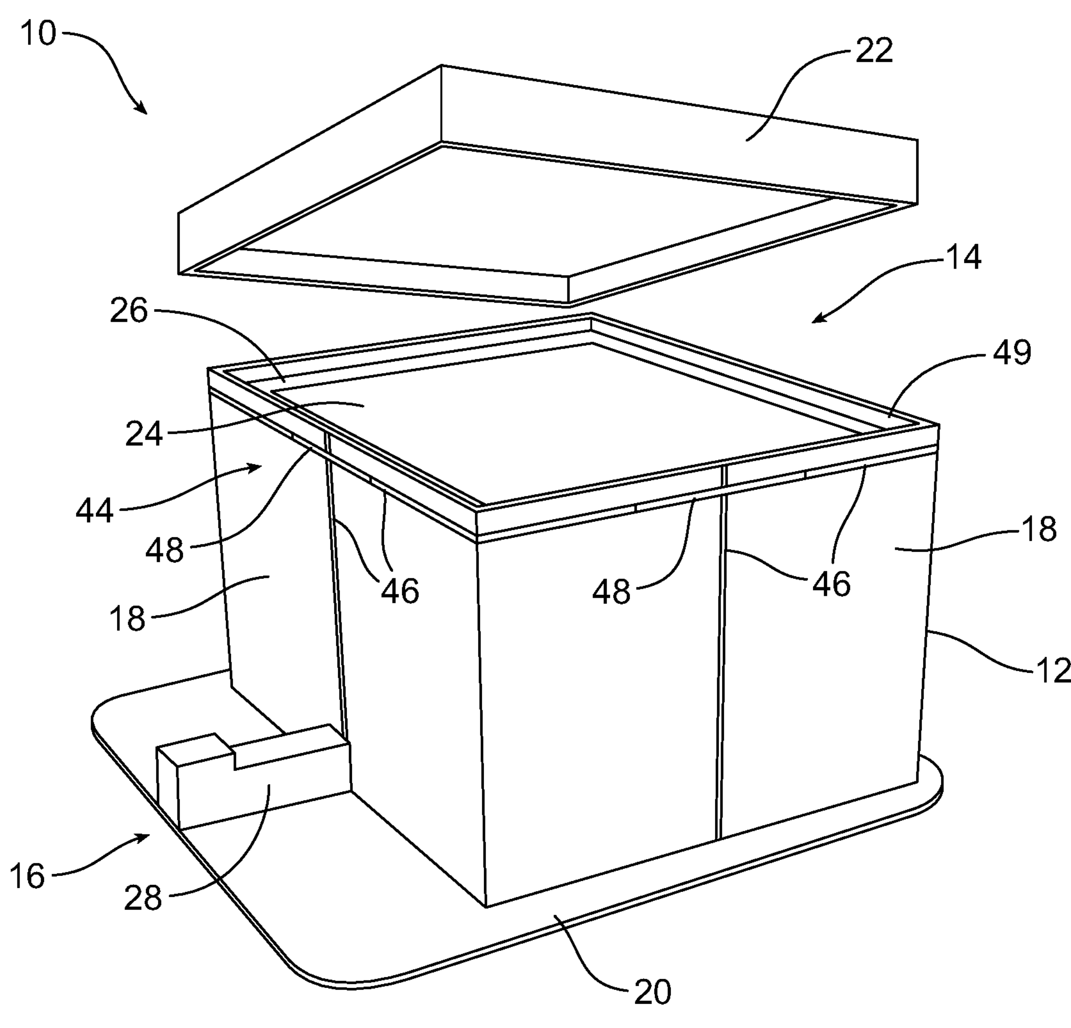
FIG. 2 is a perspective view of the housing, the image plate and the image capture assembly of the new quality assurance system.

Reference is now made to FIG. 1 illustrating the new and improved quality assurance system 10 and a medical accelerator M. As illustrated, the medical accelerator M includes a gantry G supported for rotation with respect to a stand S. A treatment head H carried on the gantry G directs radiation toward a target located at the isocentre I. Room lasers L function to identify the isocentre I. As illustrated in FIG. 1, the quality assurance system 10 has been positioned on the treatment couch C of the medical accelerator M at the isocentre I using the room lasers L as a guide.

Reference is now made to FIGS. 2-5 illustrating the new quality assurance system 10 adapted for the measurement of a two-dimensional radiation fluence image in relation to visible and mechanical indicators. The quality assurance system 10 generally includes a housing 12, an image plate 14 and an image capture assembly 16.

The housing 12 includes a sidewall 18. In the illustrated embodiment, the sidewall 18 has four sides. The sidewall 18 sits on a base 20 and has an open top. The image plate 14 is supported by the sidewall 18 so as to extend completely across the open top. The housing 12 also includes a removable lid 22, the function of which will be described in detail below.

The housing 12, including the lid 22, may be made from an opaque material so as to block the transmission of external ambient light from the room onto the image plate 14 and into the interior of the housing 12. At least the lid 22 is made from a radiation build up material. For purposes of this document, "radiation build up material" means a material that is placed on the surface of a material or patient that increases the intensity of the radiation. Examples of a radiation build up material include, but are not necessarily limited to plastic or metal sheets for flat surfaces and wet gauze or flexible tissue equivalent sheets such as "super flab" for patients.

The image plate 14 is adapted to display both a visible field image and a radiation field image as generated by the medical accelerator MA undergoing quality assurance testing. Toward this end, the image plate 14 may comprise a semi-transparent phosphor screen 24 that is supported on an optically clear sheet 26 of clear polystyrene, acrylic or other appropriate material. That sheet 26 may be, for example, 2 cm thick in order to provide structural rigidity to the image plate 14. The visible light image reproduction of the radiation field generated by the medical accelerator is produced by the radiation interaction with the phosphor molecules embedded on the screen 24, which responds in real time to changes in the radiation. As such, the system 10 is capable of collecting static, as well as video images of a dynamic radiation beam.

The image capture assembly 16 may be said to generally comprise a shroud 28 of opaque material that is connected to and is effectively an extension of the housing 12. In one possible embodiment of the system 10 illustrated in FIG. 4, the image capture assembly 16 is a small form factor optical tunnel (SFFOT) that includes (a) an image capture lens 30, (b) a mirror 32, (c) an optical tunnel 33, having two achromatic doublets 34, 36, and (d) a camera sensor 38 of a type known in the art. Note IP represents an illustration of the image path.

The lens 30 is positioned within the housing 12 below the image plate 14 and focused upon the underside of the image plate from which the lens may capture an image. The semi-transparent nature of the phosphor screen 24 and the optically clear sheet 26 allow visible field images projected from the overlying head H of the medical accelerator M to be visible to the capture lens 30. Further, the phosphor screen 24 also functions to convert the radiation field generated and emitted from the head H of the medical accelerator M into a corresponding visible light reproduction of the radiation field that is visible to the capture lens 30.

The mirror 32 of the illustrated embodiment is a 90 degree mirror adapted to redirect the captured image received from the lens 30 outward from the housing 12 through the optical tunnel 33 shielded from ambient light by the shroud 28. The two achromatic doublets 34, 36 of the optical tunnel 33 function to propagate the captured images from the mirror 32 to the camera sensor 38 which detects and records the captured images. That camera sensor 38 may be connected by a signal cable 40 to a computing device 42.

The computing device 42 is adapted to do one or more of the following: (a) control the camera sensor 38, (b) store the images captured by the lens 30 and recorded by the camera sensor, (c) compare the visible light field image and the visible light image reproduction of the radiation field to determine proper coincidence, (d) display the visible light field and the visible light image reproduction of the radiation field in real time and (e) collect and analyze data respecting the radiation field generated by the medical accelerator. The computing device 42 may comprise one or more processors, one or more memories and one or more network interfaces all in communication with each other over a communication bus. In one or more embodiments, the computing device 42 may comprise a dedicated microprocessor or electronic control unit (ECU) operating in accordance with instructions from appropriate control software.

As illustrated in FIG. 5, a locator feature 44 including alignment markings (e.g. cross hairs) 46 and a cooperating locator window 48 may be provided on the side of the image plate 14. The locator feature 44 may comprise alignment markings 46 and a cooperating locator window 48 on each facet 14*a*, 14*b*, 14*c* and 14*d* of an opaque frame 49 outlining the edges of the image plate 14. Each window 48 may comprise a narrow slot of perhaps 5 cm in width and 0.5 cm in height. Each window 48 penetrates through the frame 49 of the image plate 14 and is adapted to transmit laser light from the alignment lasers L of the medical accelerator M upon the face and/or the edge of the image plate 14.

As will be explained in greater detail below, this locator feature 44 allows the housing 12 and the image plate 14 of the system 10 to be properly positioned on the couch C of the medical accelerator M for purposes of completing quality assurance analysis. When the housing 12 and image plate 14 supported thereon are properly aligned, the alignment lasers L and the cross-hairs CH are visible from the interior optical system through the locator windows 46. The vertical laser L produces a line of laser light across the central portion of the image screen 14. The horizontal laser L produces a diffuse illumination and bright edge intensity of laser light when the system is properly positioned at isocenter I.

As illustrated in FIG. 6, the quality assurance system 10 also includes a calibration template 50 in the form of indica 52 printed upon a thin sheet 54 of light permeable material. In the illustrated embodiment, the indica 52 include dots 54 outlining an outer field boundary 55 and dots 56 outlining an inner square 57. Also note how the middle dots 58 in the outer field boundary 55 and the inner square 57 allow alignment with the cross hairs CH that are projected from the overlying gantry G of the medical accelerator M so as to allow for and confirm proper alignment between the housing 12 of the system 10 and the medical accelerator M.

The quality assurance system 10 is useful in a new and improved method of assuring proper performance of a medical accelerator M adapted to generate a visible light field and a radiation field. That method may be said to include the steps of:

(i) positioning a housing 12 and an image plate 14 of the quality assurance system 10 in proper position on a couch C of the medical accelerator M by aligning alignment markings 46 of the quality assurance system with alignment lasers L of the medical accelerator;

(ii) displaying on the image plate a visible light field image and a radiation field image generated by the medical accelerator; and (iii) capturing the visible light field image and the radiation field image displayed by the image plate.

The method may also include the step transmitting the visible light field image generated by the medical accelerator M through the image plate 14. In one or more embodiments, the method may also include the step of converting the radiation field generated by the medical accelerator into a corresponding visible light image reproduction of the radiation field generated by the medical accelerator. Still further, the method may include the step of displacing a lid 22 of the quality assurance system 10 between a radiation field image gathering position covering the image plate 14 and a visible light field image gathering position exposing the image plate.

Reference is now made to FIGS. 4-7B to further explain the use and operation of the system 10 and the related method. The initial hardware set-up of the quality assurance system 10 may be summarized as follows:

Power Up

- Attach the computing device/laptop 42 to the input side of the power over Ethernet (POE) via Gig-e cable (short).
- Plug the POE injector into a power outlet
- Attach quality assurance system input to the output of the POE injector via Gige cable (long).
- Log in to the dedicated laptop
- Confirm that the laptop and control software are active (See Software Set-up below)

Initial Positioning

- Position housing 12 and image plate 14 on treatment couch C and align to room lasers L and cross hair CH such that the top surface of the image plate 14 is located at the plane of isocenter I and is centered.
- Set the linac gantry angle of the medical accelerator M such that the beam points straight down and the collimator setting is in its neutral position, e.g. 0 degrees.
- Set a 10 cm×10 cm field and use the alignment template 50 to adjust the housing 12 and image plate 14 so that the template aligns with the edges of the light field.
- Collect an image of the light field and cross hairs using the Image capture module in the control software.
- Import the image into the control software and turn on the Display calibration template function.
- Assess the alignment of the housing and image plate and adjust as needed.
- Collect 2 images with the gantry rotated by + and −45 degrees. Assess the movement of the center of the cross hairs upon rotation. If the surface is located at the isocenter plane, the cross-hair center will remain stationary upon rotation. If the surface is not located at the isocenter plane, the intersection of the cross hairs will move upon rotation.

Initial Hardware Set-Up Checklist

- Lasers L are lined up on both sides with the alignment markings/external indicators 46 in up/down and in/out directions
- Collimator cross-hairs are aligned with the calibration template 50 in the left/right, in/out directions
- Collimator cross-hairs are stationary when gantry is rotated by +/−45 degrees.

Software Set-Up Checklist

- Computing device/Laptop computer 42 turns on, control software launches and camera 38 is connected
- Live image stream is visible in the Camera Controls menu and images can be saved to disk
- Image is adjusted for Gain, Exposure control and Black level so that the image has good brightness without being saturated
- Electronic cross hairs are visible and centered in the image window when the Crosshairs button is checked Measurement Basics Front Pointer Consistency

- Insert the front pointer P into its accessory slot AS and gently extend it downward until it touches the top surface of the image plate 14. See FIG. 7.
- The distance reading on the front pointer P should be equal to the SAD of the linac, typically 1000 mm
- Assess the results using industry standard guidelines.

Optical Distance Indicator (ODI)

- After ensuring that the top surface of the image plate 14 is at the isocenter plane, project the ODI
- Collect an image using the control software
- Assess the results using industry standard guidelines.

Light/Radiation Field Coincidence

- Project a light field of the desired size within the maximum field size measurable by the quality assurance system 10 and record an image using the control software.
- Place the removable lid 18 over the image plate 14, taking care not to move the device.
- Exit the room and irradiate the image plate 14 using the same field size. Record the image using the control software. See FIG. 8A showing the visible light image reproduction VLI of the radiation field as displayed by the phosphor screen 24 of the image plate 14.
- Run the light/radiation coincidence routine in the control software and record the agreement.
- Assess the results using industry standard guidelines.

Picket Fence Test

- With the lid 18 in place covering the image plate 14
- Irradiate the nuFilm with static images that form a picket fence test pattern and record images of each set of leaf positions.
- Import the images into the control software.
- Assess the results using industry standard guidelines.

Collimator Walk Out—Cross Hairs

- Remove the lid 18 to expose the top surface of the image plate 14 and project a visible light field of the desired size (typically 10 cm×10 cm) with the collimator cross-hairs visible and aligned properly.
- Using the control software,
  - Collect images with the collimator rotated to various angles over its range of motion.
  - Run the Walk-Out Component module in the control software
  - Use the results as input into Star Fitting Analysis
- Assess the results using industry standard guidelines.

Radiation Profile Constancy

- Ensure that the housing 12 and image plate 14 supported upon the housing are properly aligned on the treatment couch C.
- Position the lid 18 over the top surface of the image plate 14.

Apply a radiation field of an appropriate dimension and intensity, as determined by the QMP and record the image.

Import the image into the control software and run the "Profile constancy" routine, selecting the profile type (e.g., flatness/symmetry, or wedge).

Assess the results using industry standard guidelines.

Collimator Star Shot

Ensure that the housing 12 and image plate 14 supported thereon are properly aligned on the treatment couch C.

Project a long, narrow field of the desired size (typically 0.3 cm×10 cm).

Rotate the collimator to the first measurement angle, apply radiation at an appropriate dose rate and energy, and record an image.

Repeat the step above at several collimator angles spanning the limits of the collimator range. See the star-shot image SSI as displayed in visible light by the phosphor screen 24 of the image plate 14.

Import the images into the control software and run the "Star-shot component measurement" routine.

Use the results as input into Star Fitting Analysis.

Assess the results using industry standard guidelines.

This disclosure may be said to relate to the following items.

1. A quality assurance system adapted for viewing a visible light field and a radiation field generated by a medical accelerator, comprising:

a housing;

an image plate supported by the housing wherein the image plate is adapted to display a visible light field image and a radiation field generated by the medical accelerator; and an image capture assembly adapted to capture the visible light field image and the radiation field displayed by the image plate.

2. The quality assurance system of item 1, wherein the imaging plate includes a semi-transparent phosphor screen adapted to (a) transmit the visible light field image generated by the medical accelerator through the semi-transparent phosphor screen and (b) convert the radiation field generated by the medical accelerator into a corresponding visible light image reproduction of the radiation field generated by the medical accelerator.

3. The quality assurance system of item 2, wherein the image capture assembly is a small form factor optical tunnel (SFFOT) including a lens, a mirror, an optical tunnel and a camera wherein (a) the lens focuses the visible light field image and the visible light image reproduction of the radiation field, (b) the mirror redirects the visible light field image and the visible light image reproduction of the radiation field from the lens through the optical tunnel, (c) the optical tunnel propagates the visible light field image and the visible light image reproduction of the radiation field from the mirror to the camera and (d) the camera captures the visible light field image and visible light image reproduction of the radiation field.

4. The quality assurance system of any of items 1-3, wherein the housing further includes a removable lid that is displaceable between a visible light image reproduction of the radiation field gathering position covering the image plate and a visible light field image gathering position exposing the image plate.

5. The quality assurance system of item 4, wherein the removable lid is made from a radiation build up material.

6. The quality assurance system of item 4, further including a computing device adapted to do one or more of the following: (a) control the camera, (b) compare the visible light field image and the visible light image reproduction of the radiation field to determine proper coincidence, (c) display the visible light field image and the visible light image reproduction of the radiation field in real time and (d) collect and analyze data respecting the radiation field generated by the medical accelerator.

7. The quality assurance system of item 4, further including a calibration template on the imaging plate.

8. The quality assurance system of item 4, further including a locator feature including at least one locator window in a sidewall of the image plate wherein the at least one locator window is adapted to transmit laser light from an alignment laser of the medical accelerator onto the image plate.

9. The quality assurance system of item 8, wherein the at least one locator window is exposed when the removable lid is in the visible light field gathering position and the at least one locator window is covered by the removable lid when the removable lid is in the radiation field image gathering position.

10. The quality assurance system of item 9, wherein the locator feature further includes a prism associated with the at least one locator window.

11. The quality assurance system of item 10, further including further including alignment markings on the image plate, the housing or the image plate and the housing, said alignment markings being adapted to allow for alignment of the image plate with the alignment laser of the medical accelerator.

12. The quality assurance system of item 11, wherein the housing and the optical tunnel are opaque.

13. The quality assurance system of item 4, further including a computing device adapted to do one or more of the following: (a) control the camera, (b) compare the visible light field image and the visible light image reproduction of the radiation field to determine proper coincidence, (c) display the visible light field and the visible light image reproduction of the radiation field in real time and (d) collect and analyze data respecting the radiation field generated by the medical accelerator.

14. A quality assurance system for a medical accelerator adapted to generate a visible light field and a radiation field, comprising:

a housing;

an image plate supported by the housing; and an image capture assembly wherein the housing further includes a removable lid that is displaceable between a radiation field image gathering position covering the image plate and a visible light field image gathering position exposing the image plate.

15. The quality assurance system of item 14, further including a locator feature including at least one locator window in a sidewall of the image plate, the housing or the image plate and the housing wherein the at least one locator window is adapted to transmit laser light from an alignment laser of the medical accelerator onto the image plate.

16. The quality assurance system of item 15, wherein the at least one locator window is exposed when the removable lid is in the visible light field gathering position and the at least one locator window is covered by the removable lid when the removable lid is in the radiation field image gathering position.

17. The quality assurance system of item 16, wherein the locator feature further includes a prism associated with the at least one locator window.

18. The quality assurance system of item 17, further including alignment markings on the image plate, the housing or the image plate and the housing, said alignment markings being adapted to allow for alignment of the image plate with the alignment laser of the medical accelerator.

19. A method of assuring proper performance of a medical accelerator adapted to generate a visible light field and a radiation field, comprising:

positioning a housing and an image plate of a quality assurance system in proper position on a couch of a medical accelerator by aligning alignment markings of the quality assurance system with alignment lasers of the medical accelerator;

displaying on the image plate a visible light field image and a radiation field image generated by the medical accelerator; and capturing the visible light field image and the radiation field image displayed by the image plate.

20. The method of item 19, further including (a) transmitting the visible light field image generated by the medical accelerator through the image plate and (b) converting the radiation field generated by the medical accelerator into a corresponding visible light image reproduction of the radiation field generated by the medical accelerator.

21. The method of item 20, further including displacing a lid of the quality assurance system between a radiation field image gathering position covering the image plate and a visible light field image gathering position exposing the image plate.

Each of the following terms written in singular grammatical form: "a", "an", and "the", as used herein, means "at least one", or "one or more". Use of the phrase "One or more" herein does not alter this intended meaning of "a", "an", or "the". Accordingly, the terms "a", "an", and "the", as used herein, may also refer to, and encompass, a plurality of the stated entity or object, unless otherwise specifically defined or stated herein, or, unless the context clearly dictates otherwise. For example, the phrase: "a locator feature", as used herein, may also refer to, and encompass, a plurality of locator features.

Each of the following terms: "includes", "including", "has", "having", "comprises", and "comprising", and, their linguistic/grammatical variants, derivatives, or/and conjugates, as used herein, means "including, but not limited to", and is to be taken as specifying the stated component(s), feature(s), characteristic(s), parameter(s), integer(s), or step(s), and does not preclude addition of one or more additional component(s), feature(s), characteristic(s), parameter(s), integer(s), step(s), or groups thereof.

The phrase "consisting of", as used herein, is closed-ended and excludes any element, step, or ingredient not specifically mentioned. The phrase "consisting essentially of", as used herein, is a semi-closed term indicating that an item is limited to the components specified and those that do not materially affect the basic and novel characteristic(s) of what is specified.

Terms of approximation, such as the terms about, substantially, approximately, etc., as used herein, refers to ±10% of the stated numerical value.

Although the quality assurance system 10 and related method of this disclosure have been illustratively described and presented by way of specific exemplary embodiments, and examples thereof, it is evident that many alternatives, modifications, or/and variations, thereof, will be apparent to those skilled in the art. For Example, as illustrated in FIG. 9, a prism 100 may be positioned between the locator windows 48 at the sides of the phosphor screen 24 of the image plate 14 to enhance the visibility of the lasers L and cross hairs CH on the phosphor screen. In some embodiments, mirrors could serve a similar purpose. It is intended that all such alternatives, modifications, or/and variations, fall within the spirit of, and are encompassed by, the broad scope of the appended claims.

What is claimed:

1. A quality assurance system adapted for viewing a visible light field and a radiation field generated by a medical accelerator, comprising:

a housing;

an image plate supported by the housing wherein the image plate is adapted to display a visible light field image and a radiation field generated by the medical accelerator; and an image capture assembly adapted to capture the visible light field image and the radiation field displayed by the image plate wherein the housing further includes a removable lid that is displaceable between a radiation field image gathering position covering the image plate and a visible light field image gathering position exposing the image plate.

2. The quality assurance system of claim 1, wherein the imaging plate includes a semi-transparent phosphor screen adapted to (a) transmit the visible light field image generated by the medical accelerator through the semi-transparent phosphor screen and (b) convert the radiation field generated by the medical accelerator into a corresponding visible light image reproduction of the radiation field generated by the medical accelerator.

3. The quality assurance system of claim 2, wherein the image capture assembly is a small form factor optical tunnel (SFFOT) including a lens, a mirror, an optical tunnel and a camera wherein (a) the lens focuses the visible light field image and the visible light image reproduction of the radiation field, (b) the mirror redirects the visible light field image and the visible light image reproduction of the radiation field from the lens through the optical tunnel, (c) the optical tunnel propagates the visible light field image and the visible light image reproduction of the radiation field from the mirror to the camera and (d) the camera captures the visible light field image and visible light image reproduction of the radiation field.

4. The quality assurance system of claim 3, wherein the removable lid is made from a radiation build up material.

5. The quality assurance system of claim 3, further including a computing device adapted to do one or more of the following: (a) control the camera, (b) compare the visible light field image and the visible light image reproduction of the radiation field to determine proper coincidence, (c) display the visible light field image and the visible light image reproduction of the radiation field in real time and (d) collect and analyze data respecting the radiation field generated by the medical accelerator.

6. The quality assurance system of claim 3, further including a calibration template on the imaging plate.

7. The quality assurance system of claim 3, further including a locator feature including at least one locator window in a sidewall of the image plate wherein the at least one locator window is adapted to transmit laser light from an alignment laser of the medical accelerator onto the image plate.

8. The quality assurance system of claim 7, wherein the at least one locator window is exposed when the removable lid is in the visible light field gathering position and the at least one locator window is covered by the removable lid when the removable lid is in the radiation field image gathering position.

9. The quality assurance system of claim 8, wherein the locator feature further includes a prism associated with the at least one locator window.

10. The quality assurance system of claim 9, further including further including alignment markings on the image plate, the housing or the image plate and the housing, said alignment markings being adapted to allow for alignment of the image plate with the alignment laser of the medical accelerator.

11. The quality assurance system of claim 10, wherein the housing and the optical tunnel are opaque.

12. The quality assurance system of claim 3, further including a computing device adapted to do one or more of the following: (a) control the camera, (b) compare the visible light field image and the visible light image reproduction of the radiation field to determine proper coincidence, (c) display the visible light field and the visible light image reproduction of the radiation field in real time and (d) collect and analyze data respecting the radiation field generated by the medical accelerator.

13. A quality assurance system for a medical accelerator adapted to generate a visible light field and a radiation field, comprising:

a housing;

an image plate supported by the housing; and an image capture assembly wherein the housing further includes a removable lid that is displaceable between a radiation field image gathering position covering the image plate and a visible light field image gathering position exposing the image plate.

14. The quality assurance system of claim 13, further including a locator feature including at least one locator window in a sidewall of the image plate, the housing or the image plate and the housing wherein the at least one locator window is adapted to transmit laser light from an alignment laser of the medical accelerator onto the image plate.

15. The quality assurance system of claim 14, wherein the at least one locator window is exposed when the removable lid is in the visible light field gathering position and the at least one locator window is covered by the removable lid when the removable lid is in the radiation field image gathering position.

16. The quality assurance system of claim 15, wherein the locator feature further includes a prism associated with the at least one locator window.

17. The quality assurance system of claim 16, further including alignment markings on the image plate, the housing or the image plate and the housing, said alignment markings being adapted to allow for alignment of the image plate with the alignment laser of the medical accelerator.

18. A method of assuring proper performance of a medical accelerator adapted to generate a visible light field and a radiation field, comprising:

positioning a housing and an image plate of a quality assurance system in proper position on a couch of a medical accelerator by aligning alignment markings of the quality assurance system with alignment lasers of the medical accelerator;

displaying on the image plate a visible light field image and a radiation field image generated by the medical accelerator;

capturing the visible light field image and the radiation field image displayed by the image plate;

transmitting the visible light field image generated by the medical accelerator through the image plate;

converting the radiation field generated by the medical accelerator into a corresponding visible light image reproduction of the radiation field generated by the medical accelerator; and displacing a lid of the quality assurance system between a radiation field image gathering position covering the image plate and a visible light field image gathering position exposing the image plate.

* * * * *